United States Patent
DeJong et al.

(10) Patent No.: US 7,202,330 B2
(45) Date of Patent: Apr. 10, 2007

(54) RGD (ARG-GLY-ASP) COUPLED TO (NEURO)PEPTIDES

(75) Inventors: Marion DeJong, Vlaardingen (NL); Eric Paul Krenning, Rotterdam (NL); Petrus Martinus Van Hagen, Rotterdam (NL)

(73) Assignee: BioSynthema Inc., St. Louis, MO (US)

( * ) Notice: Subject to any disclaimer, the term of this patent is extended or adjusted under 35 U.S.C. 154(b) by 614 days.

(21) Appl. No.: 10/258,766

(22) PCT Filed: Apr. 26, 2001

(86) PCT No.: PCT/EP01/04764

§ 371 (c)(1),
(2), (4) Date: Feb. 24, 2003

(87) PCT Pub. No.: WO01/81426

PCT Pub. Date: Nov. 1, 2001

(65) Prior Publication Data

US 2004/0136907 A1   Jul. 15, 2004

(30) Foreign Application Priority Data

Apr. 26, 2000   (EP) ................................. 00201499

(51) Int. Cl.
*C07K 7/64* (2006.01)
*A61K 38/12* (2006.01)
*A61K 51/08* (2006.01)

(52) U.S. Cl. .................... 530/311; 530/317; 424/1.45; 514/9

(58) Field of Classification Search .................... None
See application file for complete search history.

(56) References Cited

FOREIGN PATENT DOCUMENTS

| EP | 0385659 | 2/1990 |
|---|---|---|
| WO | PCT/EP01/04764 | 2/2002 |

OTHER PUBLICATIONS

Trulsson et al., Cholecystokinin octapeptide induces both proliferation and apoptosis in the rat pancreas, Regul. Pept., 98(1-2):41-48, Apr. 2, 2001.*
Karki et al., Arch. Of Biochem. & Biophys., Kinetic comparison of procaspase-3 and caspase 3, 442:125-32, 2005.*
Huang et al., Chemistry & Biology, Jul. 7, 2000(7):453-61.*
Buckley, Christopher D., Pilling, Darrell, Henriquez, Nick V., Parsonage, Greg, Threlfall, Katy, Scheel-Teollner, Dagmar, Simmons, David L., Akbar, Arne N., Lord, Janet M., Salmon, Mike; *RGD Peptides Induce Apoptosis by Direct Caspase-3 Activiation*; Nature; Feb. 11, 1999; pp. 534-539; vol. 397; Macmillan Magazines, Ltd.
DeJong, Marion, Breeman, W.A.P., Bernard, H.F., Kooij, P.P.M., Slooter, G.D., Van Eijck, C.H.J., Kwekkeboom, D.J., Valkema, R., Macke, H.R., Krenning, E.P.; *Therapy of Neuroendocrine Tumors with Radiolabeled Somatostatin-Analogues*; Quarterly Journal of Nuclear Medicine; 1999; pp. 356-365; vol. 43, No. 4.
Vella, F., Hernandez, J.F., Molla, A., Block, M.R., Arlaud, G.J.; *Grafting An RGD Motif Onto An Epidermal Growth Factor-like Module: Chemical Synthesis and Functional Characterization of the Chimeric Molecule*; Journal of Peptide Research; 1999; pp. 415-426; vol. 54.
Humphries et al., A Synthetic Peptide from Fibronectic Inhibits Experimental Mestasis of Murine Melanoma Cells, Science, 1986, pp. 467-470.
Ferguson, et al., Two integrin-binding peptides abrogate T cell-mediated immune responses in vivo, Proc Natl Acad Sci, 1991, pp. 8072-8076, vol. 88.
Brooks et al., Integrin Antagonists Promote Tumor Regression by Inducing Apoptosis of Angiogenic Blood Vessels, Cell, 1994, pp. 1157-1164, vol. 79.
Boucaut et al., Biologically Active Synthetic Peptides as Probes of Embryonic Development: A Competitive Peptide Inhibitor of Fibronectin Function Inhibits Gastrulation in Amphibian Embryos and Neural Crest Cell Migration in Avian Embryos, J Cell Biol, 1984, pp. 1822-1830, vol. 99.
Capello et al., Increased Cell Death After Therapy with an Arg-Gly-Asp-Linked Somatostatin Analog, J Nucl Med, 2004, pp. 1716-1720, vol. 45.
van Hagen et al., "Evaluation of a radiolabelled cyclic DTPA-RGD analogue for tumour imaging and radionuclide therapy." Int J Cancer. Aug. 20, 2000;90(4):186-98.
Bernard et al., "Radiolabeled RGD-DTPA-Tyr3-octreotate for receptor-targeted radionuclide therapy." Cancer Biother Radiopharm. Apr. 2004;19(2):173-80.
Capello et al., "Anticancer activity of targeted proapoptotic peptides." J Nucl Med. Jan. 2006;47(1):122-9.

* cited by examiner

*Primary Examiner*—Elizabeth Kemmerer
*Assistant Examiner*—Kimberly A. Ballard
(74) *Attorney, Agent, or Firm*—Thompson Coburn LLP

(57) ABSTRACT

The invention relates to compounds having a binding affinity for both the αvβ3 receptor and a (neuro)peptide receptor, in particular the somatostatin receptor, which compound comprises a first peptide part comprising at least once the amino acid sequence Arg-Gly-Asp, and a second peptide part coupled thereto, optionally via a linker, which second peptide part is a (neuro)peptide.

8 Claims, No Drawings

RGD (ARG-GLY-ASP) COUPLED TO (NEURO)PEPTIDES

APPLICATION CROSS-REFERENCES

This application claims priority of International Application Number PCT/EPO01/04764, filed Apr. 26, 2001, which in turn claims priority from European Application No. 00201499.1, filed Apr. 26, 2000.

The present invention relates to compounds that have a binding affinity for both the αvβ3 receptor and a (neuro) peptide receptor, in particular the somatostatin receptor.

The integrin αvβ3 receptor is predominantly expressed in growing and migrating endothelial cells, and has been identified as a marker of the angiogenic phenotype of vascular cells during e.g. tumor angiogenesis. The αvβ3 integrin itself is expressed by tumor cells as well. The αvβ3 receptor is thus a potential target for tumor seeking molecules.

Another type of receptor that occurs in tumors are the somatostatin receptors. Their presence has been demonstrated in a variety of tumors and also on immune cells by classical biochemical binding techniques, autoradiography, in situ hybridization and RT-PCR. Binding of a ligand to a somatostatin receptor most often results in internalization of the ligand/somatostatin-receptor complex.

The natural ligand to the somatostatin receptors is somatostatin, a 14 or 28 amino acid neuropeptide, which binds with high affinity to all 5 somatostatin receptor subtypes (sst). Somatostatin is rapidly degraded in plasma, but enzymatic degradation-stable somatostatin analogs have been developed. The clinically most widely used analogues are octreotide and lanreotide, these compounds bind with high affinity to the sst 2, 3 and 5.

It was contemplated according to the invention to combine ligands having an affinity for both types of receptors in one compound in order to improve on the overall affinity of the compound for tumors.

To this end the invention relates to compounds having a binding affinity for both the $\alpha_v\beta_3$ receptor and a (neuro) peptide receptor, in particular the somatostatin receptor, which compound comprises a first peptide part comprising at least once the amino acid sequence Arg-Gly-Asp, and a second peptide part coupled thereto, optionally via a linker, which second peptide part is a (neuro)peptide.

The invention is not only applicable to somatostatin, but also to other (neuro)peptides. Consequently, the second peptide part is preferably selected from the group consisting of CCK, gastrin, substance P, bombesine, VIP (vasoactive intestinal peptide), PACAP (pituitary adenylate cyclate activating peptide), somatostatin and analogues of these. Analogues may be modified versions of the original peptide to improve stability or activity or may be parts of the peptides that still retain their biological activity.

In a preferred embodiment, the second peptide part is a somatostatin analogue, preferably selected from the group consisting of octreotate, octreotide, lantreotide, vapreotide or derivatives thereof.

The first peptide part is a so-called RGD-peptide, which is a peptide having at least once the Arg-Gly-Asp motif. Analogues of the original RGD-peptide may comprise additional amino acids, such as Tyrosine for iodination. In a preferred embodiment of the RGD-analogue an additional Asp is present between the Tyr and the linker. This Asp serves for cyclisation of the RGD-peptide part to make it more stable.

A suitable linker is for example Lysine, which has two $NH_2$-groups. One of these can be used for coupling to the RGD-peptide while the COOH group is used for coupling to the (neuro)peptide. The remaining $NH_2$-group can then be used for coupling to a chelator. The chelator is used for complexing a (radioactive) label.

Radiolabeling of these neuropeptide-RGD compounds, either directly or via a chelator (with or without spacer), makes these compounds suitable as radiodiagnostics or radiopharmaceuticals. Suitable isotopes for radiolabeling are the following $^{213}$Bi, $^{186}$Re, $^{188}$Re, $^{77}$As, $^{90}$Y, $^{66}$Ga, $^{67}$Cu, $^{169}$Er, $^{114m}$In, $^{117m}$Sn, $^{121}$Sn, $^{127}$Te, $^{142}$Pr, $^{143}$Pr, $^{198}$Au, $^{199}$Au, $^{149}$Tb, $^{161}$Tb, $^{109}$Pd, $^{165}$Dy, $^{149}$Pm, $^{151}$Pm, $^{153}$Sm, $^{157}$Gd, $^{159}$Gd, $^{166}$Ho, $^{172}$Tm, $^{169}$Yb, $^{175}$Yb, $^{177}$Lu, $^{105}$Rh, $^{103m}$Rh, $^{195m}$Pt, $^{111}$Ag, $^{124}$I, $^{131}$I and $^{211}$At, $^{99m}$Tc, $^{203}$Pb, $^{67}$Ga, $^{68}$Ga, $^{72}$As, $^{111}$In, $^{113m}$In, $^{97}$Ru, $^{62}$Cu, $^{64}$Cu, $^{52}$Fe, $^{52m}$Mn, $^{51}$Cr, $^{123}$I, $^{131}$I, $^{75}$Br, $^{76}$Br, $^{77}$Br and $^{82}$Br. An example of such a radiolabeled compound is the $^{111}$In-DTPA-somatostatin analogue-RGD compound.

RGD-peptides coupled to somatostatin analogues (or other (neuro)-peptides and their analogues) may bind to and enter the cell via either the RGD-receptor (αvβ3) or one of the somatostatin receptors. With the compound binding to two different receptors, namely the (neuro)-peptide receptor and αvβ3 integrin, it can thus be expected to find the compound on different target cells like tumor cells, as well as on the cells of the tumor vascularization. This may contribute to a higher target-background ratio.

A prototype for compounds of the invention is RGD-octreotide. Octreotide is a stable peptide (resistant to plasma degradation) that binds to the somatostatin receptor (sst) subtypes 2, 3 and 5. Other compounds are as described in the examples.

It was found in autoradiography experiments with tissues having either sst-receptors or αvβ3-receptors that although both original peptides are combined in one new compound they both retain their binding affinity for their own receptors. Binding of the novel compound to the respective receptors could be blocked with an excess of the different competing analogues.

The present invention will be further illustrated in the Examples that follow and that are in no way intended to limit the invention.

EXAMPLES

Example 1

General Method for Synthesis of RGD-(Neuro)Peptides Conjugates and Their Corresponding DTPA- or DOTA-Derivatives The following is a general method for the preparation of compounds of the invention.

Solid phase peptide synthesis (SPPS) is performed using a PE Biosystems "Pioneer" synthesizer employing Fmoc strategy. A linear peptide consisting of all amino acids of the compound is prepared on a 0.1 mmol scale with Fmoc-AA$_1$ (OtBu)-PEG-PS (PE Biosystems, 0.18 mmol/g loading), wherein AA$_1$ is the C-terminal amino acid, as the starting resin. Fmoc-protected amino acids (0.4 mmol) are activated with N-[(dimethylamino)-1H-1,2r3-triazolo[4,5-b]pyridin-1-ylmethylene]-N-methylmethan-aminium hexaflurophosphate N-oxide (HATU). All the amino acids and peptide synthesis reagents were purchased commercially.

On-board amide cyclization of the peptide is achieved using the "Allyl Deblock" protocol (Pd(PPh$_3$)$_4$, N-methylmorpholine, acetic acid, chloroform) followed by 7-Azabenzotriazole-1-yloxytris(pyrrolidino)-phosphonium hexafluorophosphate (PyAOP) activation. The resin containing the protected, cyclized peptide is then removed from the instrument.

The resin is suspended in 8 mL of dimethylformamide containing 92 mg of thallium trifluoroacetate. The mixture is shaken for 2–3 hours, filtered, successively washed with 10 mL of DMF, 10 mL of DMF-water (1:1), 10 mL of DMF and THF to yield protected peptide (III) attached to the resin. The resin is then divided into two portions.

The peptide is cleaved from the resin and deprotected using 85% TFA/5% water/5% phenol/5% thianisole for 10–12 hours. The crude peptide is isolated by precipitation with t-butyl methyl ether followed by centrifugation and purified by reverse phase HPLC using an acetonitrile/water gradient containing 0.1% TFA (Solvent A: 0.1% TFA/H$_2$O, Solvent B: 0.1% TFA/10% H$_2$O/CH$_3$CN; Gradient: Hold at 95% A/5% B for 2.0 min. followed by solvent A (100%) to 50% A:50% B over a period of 20 minutes).

The Mtt protecting group of the lysine is removed by treatment with 5% TFA/5% triisopropylsilane (TIPS)/90% dichloromethane (2×30 min.). The resin is washed with dichloromethane and tetrahydrofuran and suspended in DMF (2.5 mL) containing DIEA (35 µl, 0.2 mmol). In a separate vessel, tri-t-butyl DTPA anhydride or DOTA (112 mg, 0.2 mmol) is dissolved in DMF containing HBTU/HOBt (0.2 mmol, 1.0 mL of a 0.2 mmol/mL solution) and DIEA (35 µl, 0.2 mmol) to give a 5 mL solution. After agitating for one hour, the activated DTPA derivative is added to the previously suspended resin.

The reaction is permitted to continue overnight before washing the resin with DMF and THF.

The peptide was cleaved from the resin and deprotected using 85% TFA/5% water/5% phenol/5% thianisole for 10–12 hours. The crude peptide is isolated by precipitation with t-butyl methyl ether followed by centrifugation and purified by reverse phase HPLC using an acetonitrile/water gradient containing 0.1% TFA (Solvent A: 0.1% TFA/H$_2$O, Solvent B: 0.1% TFA/10% H$_2$O/CH$_3$CN; Gradient: Hold at 95% A/5% B for 2.0 min. followed by solvent A to B over a period of 20 minutes).

Example 2

Synthesis of RGD-Octreotate (IV) and the Corresponding DTPA-Derivative (V)

In accordance with the method as described in Example 1 an RGD-octreotate and its corresponding DTPA-derivative were prepared according to the following reaction scheme:

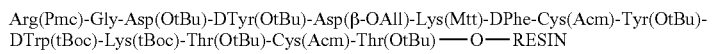
Arg(Pmc)-Gly-Asp(OtBu)-DTyr(OtBu)-Asp(β-OAll)-Lys(Mtt)-DPhe-Cys(Acm)-Tyr(OtBu)-DTrp(tBoc)-Lys(tBoc)-Thr(OtBu)-Cys(Acm)-Thr(OtBu)—O—RESIN (I)

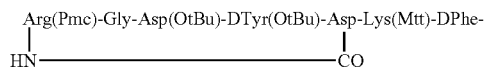
Arg(Pmc)-Gly-Asp(OtBu)-DTyr(OtBu)-Asp-Lys(Mtt)-DPhe-
HN——————————CO

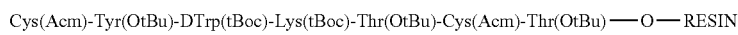
Cys(Acm)-Tyr(OtBu)-DTrp(tBoc)-Lys(tBoc)-Thr(OtBu)-Cys(Acm)-Thr(OtBu)—O—RESIN (II)

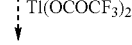
Tl(OCOCF$_3$)$_2$

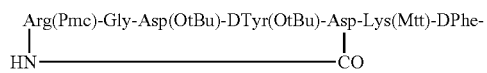
Arg(Pmc)-Gly-Asp(OtBu)-DTyr(OtBu)-Asp-Lys(Mtt)-DPhe-
HN——————————CO

Cys(Acm)-Tyr(OtBu)-DTrp(tBoc)-Lys(tBoc)-Thr(OtBu)-Cys(Acm)-Thr(OtBu)—O—RESIN
S——————————————S (III)

85% TFA, 5% H$_2$O,
5% phenol, 5% thioaniosole i. 5% TFA, 5% TIPS, 90% CH$_2$Cl$_2$
ii. tri-t-butyl mono DTPA anhydride
iii. 85% TFA, 5% H$_2$O,
  5% phenol, 5% thioaniosole (IV)  (V)

-continued

RGD-octreotate (IV):

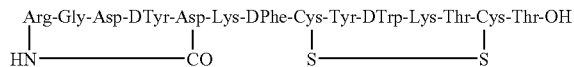

Lys(ε-DTPA)RGD-octreotate (V):

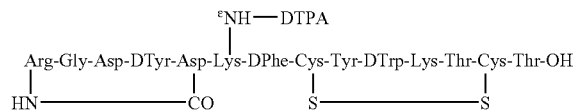

The mass spectrometer data for the RGD octreotate conjugate (IV) are as follows: Calculated 1766.6, Found: 884.8 ((M+2)/2).

The mass spectrometer data for the DTPA-derivative of the RGD-octreotate conjugate (V) are as follows: Calculated 2139.9, Found: 1071.2 ((M+2)/2).

Example 3

Synthesis of RGD-Octreotide (iv) and the Corresponding DOTA-derivative (v)

In accordance with the method as described in Example-1 an RGD-octreotide and its corresponding DTPA-derivative were prepared according to the following reaction scheme:

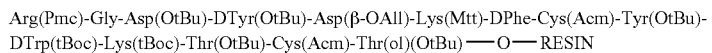

(i)

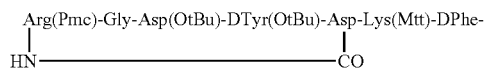

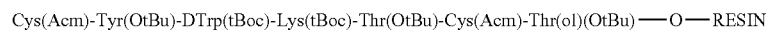

(ii)

Tl(OCOCF$_3$)$_2$

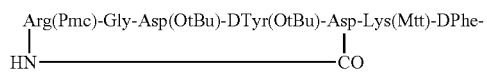

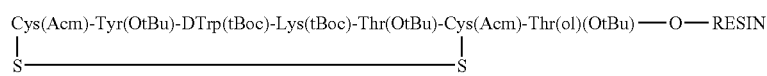

(iii)

85% TFA, 5% H$_2$O,
5% phenol, 5% thioaniosole i. 5% TFA, 5% TIPS, 90% CH$_2$Cl$_2$
ii. tri-t-butyl mono DTPA anhydride
iii. 85% TFA, 5% H$_2$O,
    5% phenol, 5% thioaniosole (iv)    (v)

RGD-octreotate (iv):

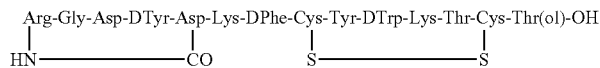

Lys(ε-DTPA)RGD-octreotate (v):

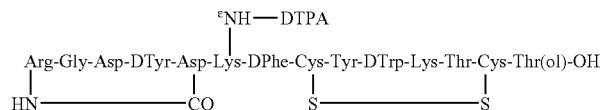

The invention claimed is:

1. A compound comprising a somatostatin receptor binding peptide or analog thereof that binds to a somatostatin receptor, a linker amino acid at the N-terminus of said somatostatin receptor binding peptide, a metal chelating group coupled to said linker and an apoptosis-inducing molecule comprising an amino acid sequence Arg-Gly-Asp-DTyr-Asp wherein the N-terminal Arg and the C-terminal Asp of said amino acid sequence are cyclized, and wherein the C-terminal Asp of said amino acid sequence is coupled to said linker amino acid.

2. The compound as in claim 1, wherein said apoptosis-inducing molecule activates Caspase-3.

3. The compound as in claim 1, wherein said somatostatin analog is selected from the group consisting of octreotate, octreotide, lantreotide, vapreotide, and derivatives thereof.

4. The compound as in claim 1, wherein said metal chelating group is a metal chelating group suitable for radiolabeling.

5. The compound as in claim 4, wherein said linker amino acid is lysine, para-amino phenylalanine, or diamino propionic acid.

6. The compound as in claim 4, wherein said metal chelating group suitable for radiolabeling is DTPA or DOTA.

7. The compound as in claim 4, wherein said metal chelating group is radiolabeled with a radioisotope selected from the group consisting of $^{213}$Bi, $^{186}$Re, $^{188}$Re, $^{77}$As, $^{90}$Y, $^{6}$Ga, $^{67}$Cu, $^{169}$Er, $^{114}$In, $^{117m}$Sn, $^{121}$Sn, $^{127}$Te, $^{142}$Pr, $^{143}$Pr, $^{198}$Au, $^{199}$Au, $^{149}$Tb, $^{161}$Tb, $^{109}$Pd, $^{165}$Dy, $^{149}$Pm, $^{151}$Pm, $^{153}$Sm, $^{157}$Gd, $^{159}$Gd, $^{166}$Ho, $^{172}$Tm, $^{169}$Yb, $^{175}$Yb, $^{177}$Lu, $^{105}$Rh, $^{103m}$Rh, $^{195m}$Pt, $^{111}$Ag, $^{124}$I, $^{131}$I, $^{121}$At, $^{99m}$Tc, $^{203}$Pb, $^{67}$Ga, $^{68}$Ga, $^{72}$As, $^{111}$In, $^{13m}$In, $^{97}$Ru, $^{62}$Cu, $^{64}$Cu, $^{52}$Fe, $^{52m}$Mn, $^{51}$Cr, $^{123}$I, $^{131}$I, $^{75}$Br, $^{76}$Br, $^{77}$Br, and $^{82}$Br.

8. The compound as in claim 6, wherein said metal chelating group is radiolabeled with a radioisotope selected from the group consisting of $^{213}$Bi, $^{186}$Re, $^{188}$Re, $^{77}$As, $^{90}$Y, $^{6}$Ga, $^{67}$Cu, $^{169}$Er, $^{114m}$In, $^{117m}$Sn, $^{121}$Sn, $^{127}$Te, $^{142}$Pr, $^{143}$Pr, $^{198}$Au, $^{199}$Au, $^{149}$Tb, $^{161}$Tb, $^{109}$Pd, $^{165}$Dy, $^{149}$Pm, $^{151}$Pm, $^{153}$Sm, $^{157}$Gd, $^{159}$Gd, $^{166}$Ho, $^{172}$Tm, $^{169}$Yb, $^{175}$Yb, $^{177}$Lu, $^{105}$Rh, $^{103m}$Rh, $^{195m}$Pt, $^{111}$Ag, $^{124}$I, $^{131}$I, $^{121}$At, $^{99m}$Tc, $^{203}$Pb, $^{67}$Ga, $^{68}$Ga, $^{72}$As, $^{111}$In, $^{13m}$In, $^{97}$Ru, $^{62}$Cu, $^{64}$Cu, $^{52}$Fe, $^{52m}$Mn, $^{51}$Cr, $^{123}$I, $^{131}$I, $^{75}$Br, $^{76}$Br, $^{77}$Br, and $^{82}$Br.

* * * * *

SEQUENCE LISTING

```
<160> NUMBER OF SEQ ID NOS: 14

<210> SEQ ID NO 1
<211> LENGTH: 14
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: Arg(Pmc)
<220> FEATURE:
<221> NAME/KEY: MOD_RES
<222> LOCATION: (3)..(3)
<223> OTHER INFORMATION: Asp(OtBu)
<220> FEATURE:
<221> NAME/KEY: MOD_RES
<222> LOCATION: (4)..(4)
<223> OTHER INFORMATION: DTyr(OtBu)
<220> FEATURE:
<221> NAME/KEY: MOD_RES
<222> LOCATION: (5)..(5)
<223> OTHER INFORMATION: Asp(beta-OAll)
<220> FEATURE:
<221> NAME/KEY: MOD_RES
<222> LOCATION: (6)..(6)
<223> OTHER INFORMATION: Lys(Mtt)
<220> FEATURE:
<221> NAME/KEY: MOD_RES
<222> LOCATION: (7)..(7)
<223> OTHER INFORMATION: DPhe
<220> FEATURE:
<221> NAME/KEY: MOD_RES
<222> LOCATION: (8)..(8)
<223> OTHER INFORMATION: Cys(Acm)
<220> FEATURE:
<221> NAME/KEY: MOD_RES
<222> LOCATION: (9)..(9)
<223> OTHER INFORMATION: Tyr(OtBu)
<220> FEATURE:
<221> NAME/KEY: MOD_RES
<222> LOCATION: (10)..(10)
<223> OTHER INFORMATION: DTrp(tBoc)
<220> FEATURE:
<221> NAME/KEY: MOD_RES
<222> LOCATION: (11)..(11)
<223> OTHER INFORMATION: Lys(tBoc)
<220> FEATURE:
<221> NAME/KEY: MOD_RES
<222> LOCATION: (12)..(12)
<223> OTHER INFORMATION: Thr(OtBu)
<220> FEATURE:
<221> NAME/KEY: MOD_RES
<222> LOCATION: (13)..(13)
<223> OTHER INFORMATION: Cys(Acm)
<220> FEATURE:
<221> NAME/KEY: MOD_RES
```

```
<222> LOCATION: (14)..(14)
<223> OTHER INFORMATION: Thr(OtBu)-O-RESIN

<400> SEQUENCE: 1

Arg Gly Asp Tyr Asp Lys Phe Cys Tyr Trp Lys Thr Cys Thr
1               5                   10

<210> SEQ ID NO 2
<211> LENGTH: 7
<212> TYPE: PRT
<213> ORGANISM: Homo sapiens
<220> FEATURE:
<221> NAME/KEY: MISC_FEATURE
<222> LOCATION: (1)..(5)
<223> OTHER INFORMATION: Amide bond between residues 1 and 5
<220> FEATURE:
<221> NAME/KEY: MOD_RES
<222> LOCATION: (1)..(1)
<223> OTHER INFORMATION: Arg(Pmc)
<220> FEATURE:
<221> NAME/KEY: MOD_RES
<222> LOCATION: (3)..(3)
<223> OTHER INFORMATION: Asp(OtBu)
<220> FEATURE:
<221> NAME/KEY: MOD_RES
<222> LOCATION: (4)..(4)
<223> OTHER INFORMATION: DTyr(OtBu)
<220> FEATURE:
<221> NAME/KEY: MOD_RES
<222> LOCATION: (6)..(6)
<223> OTHER INFORMATION: Lys(Mtt)
<220> FEATURE:
<221> NAME/KEY: MOD_RES
<222> LOCATION: (7)..(7)
<223> OTHER INFORMATION: DPhe

<400> SEQUENCE: 2

Arg Gly Asp Tyr Asp Lys Phe
1               5

<210> SEQ ID NO 3
<211> LENGTH: 7
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: Cys(Acm)
<220> FEATURE:
<221> NAME/KEY: MOD_RES
<222> LOCATION: (2)..(2)
<223> OTHER INFORMATION: Tyr(OtBu)
<220> FEATURE:
<221> NAME/KEY: MOD_RES
<222> LOCATION: (3)..(3)
<223> OTHER INFORMATION: DTrp(tBoc)
<220> FEATURE:
<221> NAME/KEY: MOD_RES
<222> LOCATION: (4)..(4)
<223> OTHER INFORMATION: Lys(tBoc)
<220> FEATURE:
<221> NAME/KEY: MOD_RES
<222> LOCATION: (5)..(5)
<223> OTHER INFORMATION: Thr(OtBu)
<220> FEATURE:
<221> NAME/KEY: MOD_RES
<222> LOCATION: (6)..(6)
<223> OTHER INFORMATION: Cys(Acm)
<220> FEATURE:
<221> NAME/KEY: MOD_RES
<222> LOCATION: (7)..(7)
<223> OTHER INFORMATION: Thr(OtBu)-O-RESIN

<400> SEQUENCE: 3
```

-continued

```
Arg Gly Asp Tyr Asp Lys Phe
1               5

<210> SEQ ID NO 4
<211> LENGTH: 7
<212> TYPE: PRT
<213> ORGANISM: Homo sapiens
<220> FEATURE:
<221> NAME/KEY: MISC_FEATURE
<222> LOCATION: (1)..(5)
<223> OTHER INFORMATION: Amide bond between residues 1 and 5
<220> FEATURE:
<221> NAME/KEY: MOD_RES
<222> LOCATION: (1)..(1)
<223> OTHER INFORMATION: Arg(Pmc)
<220> FEATURE:
<221> NAME/KEY: MOD_RES
<222> LOCATION: (3)..(3)
<223> OTHER INFORMATION: Asp(OtBu)
<220> FEATURE:
<221> NAME/KEY: MOD_RES
<222> LOCATION: (4)..(4)
<223> OTHER INFORMATION: DTyr(OtBu)
<220> FEATURE:
<221> NAME/KEY: MOD_RES
<222> LOCATION: (6)..(6)
<223> OTHER INFORMATION: Lys(Mtt)
<220> FEATURE:
<221> NAME/KEY: MOD_RES
<222> LOCATION: (7)..(7)
<223> OTHER INFORMATION: DPhe

<400> SEQUENCE: 4

Arg Gly Asp Tyr Asp Lys Phe
1               5

<210> SEQ ID NO 5
<211> LENGTH: 7
<212> TYPE: PRT
<213> ORGANISM: Homo sapiens
<220> FEATURE:
<221> NAME/KEY: DISULFID
<222> LOCATION: (1)..(6)
<223> OTHER INFORMATION:
<220> FEATURE:
<221> NAME/KEY: MOD_RES
<222> LOCATION: (1)..(1)
<223> OTHER INFORMATION: Cys(Acm)
<220> FEATURE:
<221> NAME/KEY: MOD_RES
<222> LOCATION: (2)..(2)
<223> OTHER INFORMATION: Tyr(OtBu)
<220> FEATURE:
<221> NAME/KEY: MOD_RES
<222> LOCATION: (3)..(3)
<223> OTHER INFORMATION: DTrp(tBoc)
<220> FEATURE:
<221> NAME/KEY: MOD_RES
<222> LOCATION: (4)..(4)
<223> OTHER INFORMATION: Lys(tBoc)
<220> FEATURE:
<221> NAME/KEY: MOD_RES
<222> LOCATION: (5)..(5)
<223> OTHER INFORMATION: Thr(OtBu)
<220> FEATURE:
<221> NAME/KEY: MOD_RES
<222> LOCATION: (6)..(6)
<223> OTHER INFORMATION: Cys(Acm)
<220> FEATURE:
<221> NAME/KEY: MOD_RES
<222> LOCATION: (7)..(7)
<223> OTHER INFORMATION: Thr(OtBu)-O-RESIN

<400> SEQUENCE: 5

Cys Tyr Trp Lys Thr Cys Thr
```

<210> SEQ ID NO 6
<211> LENGTH: 14
<212> TYPE: PRT
<213> ORGANISM: Homo sapiens
<220> FEATURE:
<221> NAME/KEY: DISULFID
<222> LOCATION: (8)..(13)
<223> OTHER INFORMATION:
<220> FEATURE:
<221> NAME/KEY: MISC_FEATURE
<222> LOCATION: (1)..(5)
<223> OTHER INFORMATION: Amide bond between residues 1 and 5
<220> FEATURE:
<221> NAME/KEY: MOD_RES
<222> LOCATION: (4)..(4)
<223> OTHER INFORMATION: DTyr
<220> FEATURE:
<221> NAME/KEY: MOD_RES
<222> LOCATION: (7)..(7)
<223> OTHER INFORMATION: DPhe
<220> FEATURE:
<221> NAME/KEY: MOD_RES
<222> LOCATION: (10)..(10)
<223> OTHER INFORMATION: DTrp
<220> FEATURE:
<221> NAME/KEY: MOD_RES
<222> LOCATION: (14)..(14)
<223> OTHER INFORMATION: Thr-OH

<400> SEQUENCE: 6

Arg Gly Asp Tyr Asp Lys Phe Cys Tyr Trp Lys Thr Cys Thr
 1               5                  10

<210> SEQ ID NO 7
<211> LENGTH: 14
<212> TYPE: PRT
<213> ORGANISM: Homo sapiens
<220> FEATURE:
<221> NAME/KEY: DISULFID
<222> LOCATION: (8)..(13)
<223> OTHER INFORMATION:
<220> FEATURE:
<221> NAME/KEY: MISC_FEATURE
<222> LOCATION: (1)..(5)
<223> OTHER INFORMATION: Amide bond between residues 1 and 5
<220> FEATURE:
<221> NAME/KEY: MOD_RES
<222> LOCATION: (4)..(4)
<223> OTHER INFORMATION: DTyr
<220> FEATURE:
<221> NAME/KEY: MOD_RES
<222> LOCATION: (6)..(6)
<223> OTHER INFORMATION: NH-DTPA
    [20a]
    Lys
<220> FEATURE:
<221> NAME/KEY: MOD_RES
<222> LOCATION: (7)..(7)
<223> OTHER INFORMATION: DPhe
<220> FEATURE:
<221> NAME/KEY: MOD_RES
<222> LOCATION: (10)..(10)
<223> OTHER INFORMATION: DTrp
<220> FEATURE:
<221> NAME/KEY: MOD_RES
<222> LOCATION: (14)..(14)
<223> OTHER INFORMATION: Thr-OH

<400> SEQUENCE: 7

Arg Gly Asp Tyr Asp Lys Phe Cys Tyr Trp Lys Thr Cys Thr
 1               5                  10

```
<210> SEQ ID NO 8
<211> LENGTH: 14
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: Arg(Pmc)
<220> FEATURE:
<221> NAME/KEY: MOD_RES
<222> LOCATION: (4)..(4)
<223> OTHER INFORMATION: DTyr(OtBu)
<220> FEATURE:
<221> NAME/KEY: MOD_RES
<222> LOCATION: (5)..(5)
<223> OTHER INFORMATION: Asp(beta-OAll)
<220> FEATURE:
<221> NAME/KEY: MOD_RES
<222> LOCATION: (6)..(6)
<223> OTHER INFORMATION: Lys(Mtt)
<220> FEATURE:
<221> NAME/KEY: MOD_RES
<222> LOCATION: (7)..(7)
<223> OTHER INFORMATION: DPhe
<220> FEATURE:
<221> NAME/KEY: MOD_RES
<222> LOCATION: (8)..(8)
<223> OTHER INFORMATION: Cys(Acm)
<220> FEATURE:
<221> NAME/KEY: MOD_RES
<222> LOCATION: (9)..(9)
<223> OTHER INFORMATION: Tyr(OtBu)
<220> FEATURE:
<221> NAME/KEY: MOD_RES
<222> LOCATION: (10)..(10)
<223> OTHER INFORMATION: DTrp(tBoc)
<220> FEATURE:
<221> NAME/KEY: MOD_RES
<222> LOCATION: (11)..(11)
<223> OTHER INFORMATION: Lys(tBoc)
<220> FEATURE:
<221> NAME/KEY: MOD_RES
<222> LOCATION: (12)..(12)
<223> OTHER INFORMATION: Thr(OtBu)
<220> FEATURE:
<221> NAME/KEY: MOD_RES
<222> LOCATION: (13)..(13)
<223> OTHER INFORMATION: Cys(Acm)
<220> FEATURE:
<221> NAME/KEY: MOD_RES
<222> LOCATION: (14)..(14)
<223> OTHER INFORMATION: Thr(ol)(OtBu)-O-RESIN

<400> SEQUENCE: 8

Arg Gly Asp Tyr Asp Lys Phe Cys Tyr Trp Lys Thr Cys Thr
1               5                   10

<210> SEQ ID NO 9
<211> LENGTH: 7
<212> TYPE: PRT
<213> ORGANISM: Homo sapiens
<220> FEATURE:
<221> NAME/KEY: MISC_FEATURE
<222> LOCATION: (1)..(5)
<223> OTHER INFORMATION: Amide bond between residues 1 and 5
<220> FEATURE:
<221> NAME/KEY: MOD_RES
<222> LOCATION: (1)..(1)
<223> OTHER INFORMATION: Arg(Pmc)
<220> FEATURE:
<221> NAME/KEY: MOD_RES
<222> LOCATION: (3)..(3)
<223> OTHER INFORMATION: Asp(OtBu)
<220> FEATURE:
<221> NAME/KEY: MOD_RES
<222> LOCATION: (4)..(4)
<223> OTHER INFORMATION: DTyr(OtBu)
```

```
<220> FEATURE:
<221> NAME/KEY: MOD_RES
<222> LOCATION: (6)..(6)
<223> OTHER INFORMATION: Lys(Mtt)
<220> FEATURE:
<221> NAME/KEY: MOD_RES
<222> LOCATION: (7)..(7)
<223> OTHER INFORMATION: DPhe

<400> SEQUENCE: 9

Arg Gly Asp Tyr Asp Lys Phe
1               5

<210> SEQ ID NO 10
<211> LENGTH: 7
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: Cys(Acm)
<220> FEATURE:
<221> NAME/KEY: MOD_RES
<222> LOCATION: (2)..(2)
<223> OTHER INFORMATION: Tyr(OtBu)
<220> FEATURE:
<221> NAME/KEY: MOD_RES
<222> LOCATION: (3)..(3)
<223> OTHER INFORMATION: DTrp(tBoc)
<220> FEATURE:
<221> NAME/KEY: MOD_RES
<222> LOCATION: (4)..(4)
<223> OTHER INFORMATION: Lys(tBoc)
<220> FEATURE:
<221> NAME/KEY: MOD_RES
<222> LOCATION: (5)..(5)
<223> OTHER INFORMATION: Thr(OtBu)
<220> FEATURE:
<221> NAME/KEY: MOD_RES
<222> LOCATION: (6)..(6)
<223> OTHER INFORMATION: Cys(Acm)
<220> FEATURE:
<221> NAME/KEY: MOD_RES
<222> LOCATION: (7)..(7)
<223> OTHER INFORMATION: Thr(ol)(OtBu)-O-RESIN

<400> SEQUENCE: 10

Cys Tyr Trp Lys Thr Cys Thr
1               5

<210> SEQ ID NO 11
<211> LENGTH: 7
<212> TYPE: PRT
<213> ORGANISM: Homo sapiens
<220> FEATURE:
<221> NAME/KEY: MISC_FEATURE
<222> LOCATION: (1)..(5)
<223> OTHER INFORMATION: Amide bond between residues 1 and 5
<220> FEATURE:
<221> NAME/KEY: MOD_RES
<222> LOCATION: (1)..(1)
<223> OTHER INFORMATION: Arg(Pmc)
<220> FEATURE:
<221> NAME/KEY: MOD_RES
<222> LOCATION: (3)..(3)
<223> OTHER INFORMATION: Asp(OtBu)
<220> FEATURE:
<221> NAME/KEY: MOD_RES
<222> LOCATION: (4)..(4)
<223> OTHER INFORMATION: DTyr(OtBu)
<220> FEATURE:
<221> NAME/KEY: MOD_RES
<222> LOCATION: (6)..(6)
<223> OTHER INFORMATION: Lys(Mtt)
<220> FEATURE:
```

```
<221> NAME/KEY: MOD_RES
<222> LOCATION: (7)..(7)
<223> OTHER INFORMATION: DPhe

<400> SEQUENCE: 11

Arg Gly Asp Tyr Asp Lys Phe
1               5

<210> SEQ ID NO 12
<211> LENGTH: 7
<212> TYPE: PRT
<213> ORGANISM: Homo sapiens
<220> FEATURE:
<221> NAME/KEY: DISULFID
<222> LOCATION: (1)..(6)
<223> OTHER INFORMATION:
<220> FEATURE:
<221> NAME/KEY: MOD_RES
<222> LOCATION: (1)..(1)
<223> OTHER INFORMATION: Cys(Acm)
<220> FEATURE:
<221> NAME/KEY: MOD_RES
<222> LOCATION: (2)..(2)
<223> OTHER INFORMATION: Tyr(OtBu)
<220> FEATURE:
<221> NAME/KEY: MOD_RES
<222> LOCATION: (3)..(3)
<223> OTHER INFORMATION: DTrp(tBoc)
<220> FEATURE:
<221> NAME/KEY: MOD_RES
<222> LOCATION: (4)..(4)
<223> OTHER INFORMATION: Lys(tBoc)
<220> FEATURE:
<221> NAME/KEY: MOD_RES
<222> LOCATION: (5)..(5)
<223> OTHER INFORMATION: Thr(OtBu)
<220> FEATURE:
<221> NAME/KEY: MOD_RES
<222> LOCATION: (6)..(6)
<223> OTHER INFORMATION: Cys(Acm)
<220> FEATURE:
<221> NAME/KEY: MOD_RES
<222> LOCATION: (7)..(7)
<223> OTHER INFORMATION: Thr(ol)(OtBu)-O-RESIN

<400> SEQUENCE: 12

Cys Tyr Trp Lys Thr Cys Thr
1               5

<210> SEQ ID NO 13
<211> LENGTH: 14
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: DTyr
<220> FEATURE:
<221> NAME/KEY: MOD_RES
<222> LOCATION: (7)..(7)
<223> OTHER INFORMATION: DPhe
<220> FEATURE:
<221> NAME/KEY: MOD_RES
<222> LOCATION: (10)..(10)
<223> OTHER INFORMATION: DTrp
<220> FEATURE:
<221> NAME/KEY: MOD_RES
<222> LOCATION: (14)..(14)
<223> OTHER INFORMATION: Thr(ol)-OH
<220> FEATURE:
<221> NAME/KEY: DISULFID
<222> LOCATION: (8)..(13)
<223> OTHER INFORMATION:
<220> FEATURE:
<221> NAME/KEY: MISC_FEATURE
```

```
<222> LOCATION: (1)..(5)
<223> OTHER INFORMATION: Amide bond between residues 1 and 5

<400> SEQUENCE: 13

Arg Gly Asp Tyr Asp Lys Phe Cys Tyr Trp Lys Thr Cys Thr
1               5                   10

<210> SEQ ID NO 14
<211> LENGTH: 14
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: DTyr
<220> FEATURE:
<221> NAME/KEY: MOD_RES
<222> LOCATION: (6)..(6)
<223> OTHER INFORMATION: NH-DTPA
      [20a]
      Lys
<220> FEATURE:
<221> NAME/KEY: MOD_RES
<222> LOCATION: (7)..(7)
<223> OTHER INFORMATION: DPhe
<220> FEATURE:
<221> NAME/KEY: MOD_RES
<222> LOCATION: (10)..(10)
<223> OTHER INFORMATION: DTrp
<220> FEATURE:
<221> NAME/KEY: MOD_RES
<222> LOCATION: (14)..(14)
<223> OTHER INFORMATION: Thr(ol)-OH
<220> FEATURE:
<221> NAME/KEY: DISULFID
<222> LOCATION: (8)..(13)
<223> OTHER INFORMATION:
<220> FEATURE:
<221> NAME/KEY: MISC_FEATURE
<222> LOCATION: (1)..(5)
<223> OTHER INFORMATION: Amide bond between residues 1 and 5

<400> SEQUENCE: 14

Arg Gly Asp Tyr Asp Lys Phe Cys Tyr Trp Lys Thr Cys Thr
1               5                   10
```